US010401209B2

(12) United States Patent
Yarnell et al.

(10) Patent No.: US 10,401,209 B2
(45) Date of Patent: Sep. 3, 2019

(54) LIQUID LEVEL SENSING APPARATUS AND RELATED METHODS

(71) Applicant: Abbott Laboratories, Abbott Park, IL (US)

(72) Inventors: Lyle Yarnell, Allen, TX (US); Michael Shawn Murphy, Lucas, TX (US)

(73) Assignee: Abbott Laboratories, Abbott Park, IL (US)

( * ) Notice: Subject to any disclaimer, the term of this patent is extended or adjusted under 35 U.S.C. 154(b) by 139 days.

(21) Appl. No.: 15/629,495

(22) Filed: Jun. 21, 2017

(65) Prior Publication Data

US 2017/0370759 A1    Dec. 28, 2017

Related U.S. Application Data

(60) Provisional application No. 62/353,461, filed on Jun. 22, 2016.

(51) Int. Cl.
*G01F 23/28* (2006.01)
*G01F 23/00* (2006.01)
(Continued)

(52) U.S. Cl.
CPC .......... *G01F 23/28* (2013.01); *G01F 23/0061* (2013.01); *G01N 35/1009* (2013.01);
(Continued)

(58) Field of Classification Search
CPC ......... G01N 2035/1025; G01F 23/0061–0092; G01F 23/28–2968
See application file for complete search history.

(56) References Cited

U.S. PATENT DOCUMENTS 4,577,514 A * 3/1986 Bradley ............... G01N 33/491
422/424
4,715,413 A * 12/1987 Backlund ............... G01N 30/80
141/374
(Continued)

FOREIGN PATENT DOCUMENTS

CN    1651921    8/2005
CN    1233992    12/2005
(Continued)

OTHER PUBLICATIONS

International Bureau, "International Preliminary Report on Patentability," issued in connection with International Patent Application No. PCT/US2017/038568, dated Jan. 3, 2019, 10 pages.
(Continued)

*Primary Examiner* — Peter J Macchiarolo
*Assistant Examiner* — Alexander A Mercado
(74) *Attorney, Agent, or Firm* — Hanley, Flight & Zimmerman, LLC

(57) ABSTRACT

Liquid level sensing apparatus are disclosed. An example liquid level sensing apparatus includes a cannula defining a body having a tip and an access channel. The tip to pierce a container, where the cannula is to be at least partially positioned in the container when the tip pierces the container. A probe is to be positioned in the access channel. A signal source is to electrically energize the probe and the cannula to cause the probe to emit a first signal and cause the cannula to emit a second signal.

44 Claims, 8 Drawing Sheets

(51) Int. Cl.
*G01N 35/10* (2006.01)
*H04B 1/03* (2006.01)
*G01N 1/14* (2006.01)

(52) U.S. Cl.
CPC ..... *G01N 35/1011* (2013.01); *G01N 35/1079* (2013.01); *G01N 2001/1418* (2013.01); *G01N 2035/1025* (2013.01); *G01N 2035/1093* (2013.01); *H04B 1/03* (2013.01)

(56) References Cited

U.S. PATENT DOCUMENTS

| | | | |
|---|---|---|---|
| 4,790,183 A | 12/1988 | Pfost et al. | |
| 4,841,786 A * | 6/1989 | Schulz | G01N 35/1072 73/864.25 |
| 4,912,976 A * | 4/1990 | Labriola, II | G01F 23/263 141/95 |
| 4,924,702 A | 5/1990 | Park | |
| 4,951,512 A * | 8/1990 | Mazza | G01N 35/1079 141/130 |
| 4,977,786 A * | 12/1990 | Davis | G01F 23/263 73/864.24 |
| 5,049,826 A * | 9/1991 | Sasao | G01B 7/023 324/662 |
| 5,057,823 A | 10/1991 | Dyer et al. | |
| 5,083,470 A * | 1/1992 | Davis | G01F 23/263 73/864.24 |
| 5,171,979 A | 12/1992 | Kwa et al. | |
| 5,212,992 A * | 5/1993 | Calhoun | B01L 3/021 324/690 |
| 5,262,049 A | 11/1993 | Ferkany | |
| 5,270,211 A * | 12/1993 | Kelln | G01N 35/0092 422/547 |
| 5,304,347 A * | 4/1994 | Mann | G01F 23/263 422/50 |
| 5,322,192 A | 6/1994 | Godolphin et al. | |
| 5,397,026 A | 3/1995 | Mayes | |
| 5,493,922 A * | 2/1996 | Ramey | G01F 23/266 137/392 |
| 5,506,142 A * | 4/1996 | Mahaffey | G01N 35/1004 422/547 |
| 5,507,410 A * | 4/1996 | Clark | B01F 11/0022 221/171 |
| 5,536,471 A * | 7/1996 | Clark | H01J 49/04 422/562 |
| 5,540,890 A * | 7/1996 | Clark | B01L 3/08 215/235 |
| 5,578,494 A * | 11/1996 | Clark | B01F 11/0022 215/235 |
| 5,605,665 A * | 2/1997 | Clark | H01J 49/04 220/505 |
| 5,610,069 A * | 3/1997 | Clark | B01F 11/0022 422/562 |
| 5,627,522 A * | 5/1997 | Walker | B01F 11/0022 340/618 |
| 5,641,006 A | 6/1997 | Autrey et al. | |
| 5,648,727 A * | 7/1997 | Tyberg | G01F 23/26 324/667 |
| 5,722,290 A | 3/1998 | Kronberg | |
| 5,855,851 A * | 1/1999 | Matsubara | G01F 23/263 141/130 |
| 5,935,523 A | 8/1999 | McCandless et al. | |
| 6,107,810 A | 8/2000 | Ishizawa et al. | |
| 6,148,666 A * | 11/2000 | Roesicke | G01F 23/266 340/620 |
| 6,331,437 B1 | 12/2001 | Cohen et al. | |
| 6,347,552 B1 | 2/2002 | Purpura et al. | |
| 6,413,475 B2 * | 7/2002 | Ishizawa | G01F 23/26 324/663 |
| 6,448,574 B1 | 9/2002 | Chow | |
| 6,551,558 B1 * | 4/2003 | Mann | G01F 23/24 116/109 |
| 7,024,932 B2 | 4/2006 | de Barmon et al. | |
| 7,191,647 B2 * | 3/2007 | Harazin | G01F 23/26 340/620 |
| 7,282,372 B2 | 10/2007 | VanBrunt et al. | |
| 7,377,189 B2 * | 5/2008 | Champseix | G01N 35/1079 422/68.1 |
| 7,425,303 B2 | 9/2008 | Ishizawa et al. | |
| 7,481,978 B2 | 1/2009 | Li et al. | |
| 7,603,899 B2 | 10/2009 | Li et al. | |
| 7,621,181 B2 | 11/2009 | Cammarata et al. | |
| 7,804,599 B2 | 9/2010 | Calderoni | |
| 7,977,100 B2 | 7/2011 | Itoh | |
| 7,981,383 B2 | 7/2011 | Goodale et al. | |
| 8,026,101 B2 | 9/2011 | Bower et al. | |
| 8,075,840 B2 | 12/2011 | Shimane et al. | |
| 8,100,007 B2 | 1/2012 | Elsenhans et al. | |
| 8,689,625 B2 | 4/2014 | Burkart et al. | |
| 2006/0263250 A1 * | 11/2006 | Blouin | B01L 3/021 422/63 |
| 2007/0109139 A1 * | 5/2007 | Wenzig | G01M 3/26 340/605 |
| 2008/0053216 A1 * | 3/2008 | Li | G01F 23/263 73/290 R |
| 2009/0074616 A1 | 3/2009 | Sento et al. | |
| 2010/0111384 A1 | 5/2010 | Nagai et al. | |
| 2011/0091988 A1 | 4/2011 | Itoh | |
| 2011/0102004 A1 * | 5/2011 | Schoni | G01F 23/266 324/750.01 |
| 2011/0276281 A1 * | 11/2011 | Wernet | G01F 23/241 702/55 |
| 2012/0000296 A1 * | 1/2012 | Weng | G01N 35/1011 73/863.02 |
| 2012/0180579 A1 | 7/2012 | Brady et al. | |
| 2013/0065797 A1 | 3/2013 | Silbert et al. | |
| 2013/0167613 A1 * | 7/2013 | Kokawa | G01F 25/0061 73/1.73 |
| 2013/0322200 A1 | 12/2013 | Ludwig | |
| 2014/0106467 A1 | 4/2014 | Hutter et al. | |
| 2016/0116322 A1 * | 4/2016 | Wernet | G01F 23/24 73/304 C |

FOREIGN PATENT DOCUMENTS

| | | |
|---|---|---|
| CN | 101162212 | 4/2008 |
| CN | 201397178 | 2/2010 |
| CN | 101726612 | 6/2010 |
| CN | 101526384 | 9/2010 |
| CN | 102419198 | 4/2012 |
| CN | 202204566 | 4/2012 |
| CN | 102478417 | 5/2012 |
| CN | 102928049 | 2/2013 |
| CN | 102944286 | 2/2013 |
| EP | 0223751 | 10/1991 |
| EP | 0510686 | 10/1992 |
| JP | 2000266768 | 9/2000 |
| JP | 3310380 | 8/2002 |
| JP | 3725461 | 12/2005 |
| JP | 3872486 | 1/2007 |
| JP | 2007205811 | 8/2007 |
| JP | 4117181 | 7/2008 |
| JP | 2010286325 | 12/2010 |
| JP | 2011013005 | 1/2011 |
| JP | 2011107120 | 6/2011 |
| JP | 2013190347 | 9/2013 |
| WO | 9008307 | 7/1990 |
| WO | 2006121789 | 11/2006 |
| WO | 2012012779 | 1/2012 |
| WO | 2012073922 | 7/2012 |

OTHER PUBLICATIONS

International Searching Authority, "International Search Report," issued in connection with International Application No. PCT/US2017/038568, dated Sep. 29, 2017, 6 pages.

(56) References Cited

OTHER PUBLICATIONS

International Searching Authority, "Written Opinion," issued in connection with International Application No. PCT/US2017/038568, dated Sep. 29, 2017, 8 pages.

* cited by examiner

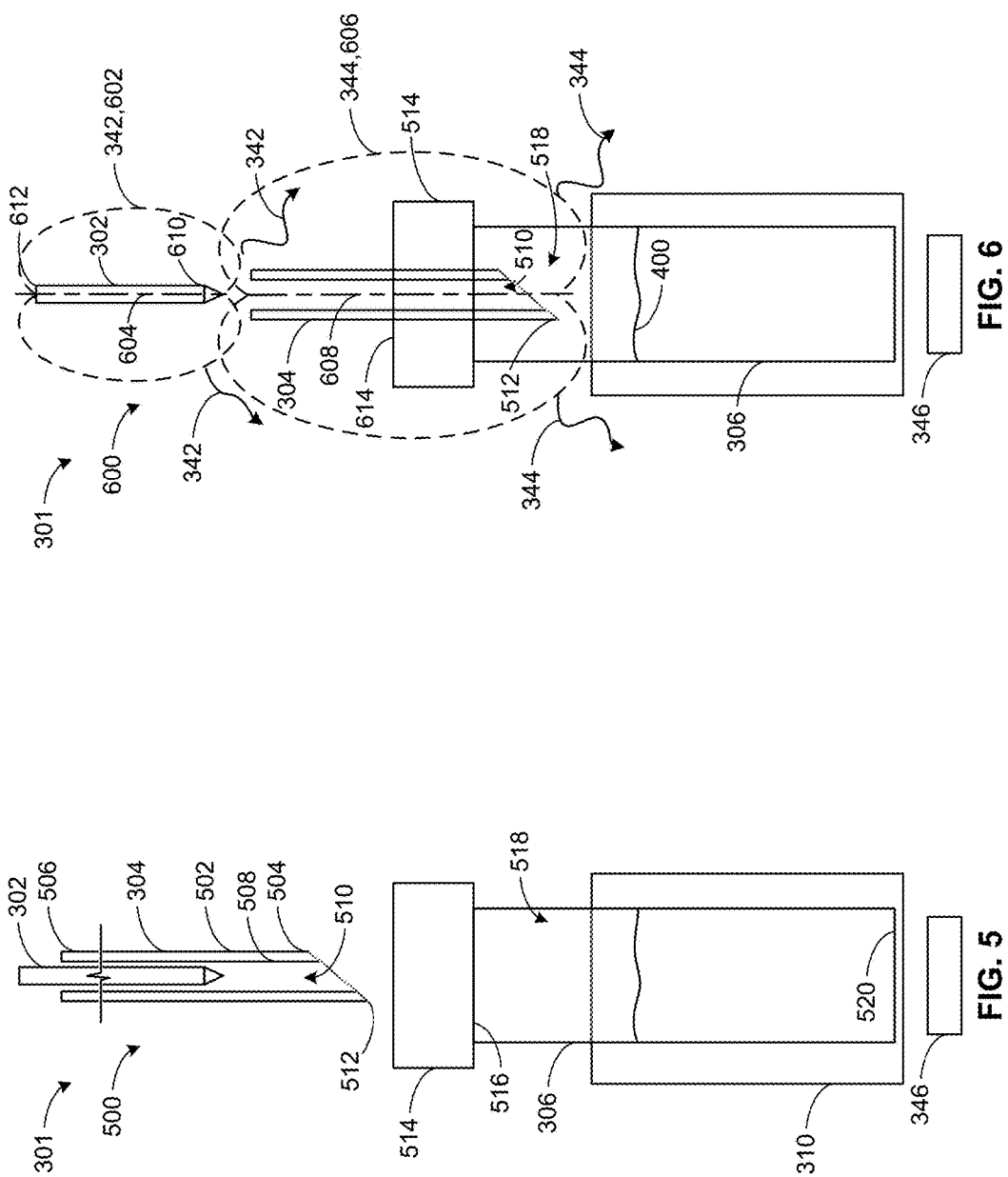

LIQUID LEVEL SENSING APPARATUS AND RELATED METHODS

CROSS-REFERENCE TO RELATED APPLICATION

This patent claims the benefit of U.S. Provisional Patent Application No. 62/353,461, filed Jun. 22, 2016, which is hereby incorporated herein by reference in its entirety.

FIELD OF THE DISCLOSURE

This disclosure relates generally to liquid level sensing systems, and, more particularly, to liquid level sensing apparatus and related methods.

BACKGROUND

Clinical chemistry and immunoassay diagnostics provide automated analyzers for processing biological fluids. Automated clinical analyzers provide rapid results with relatively high accuracy. To automate clinical chemistry and immunoassay diagnostics, analyzer systems often employ liquid sensing methods to aspirate a sample fluid from a container or test tube.

BRIEF DESCRIPTION OF THE DRAWINGS

FIGS. 5-8 illustrate schematic illustrations of the example liquid level sensing apparatus of FIGS. 2-4 at various stages of operation.

The figures are not to scale. Instead, to clarify multiple layers and regions, the thickness of the layers may be enlarged in the drawings. Wherever possible, the same reference numbers will be used throughout the drawing(s) and accompanying written description to refer to the same or like parts.

DETAILED DESCRIPTION

Figure 1:
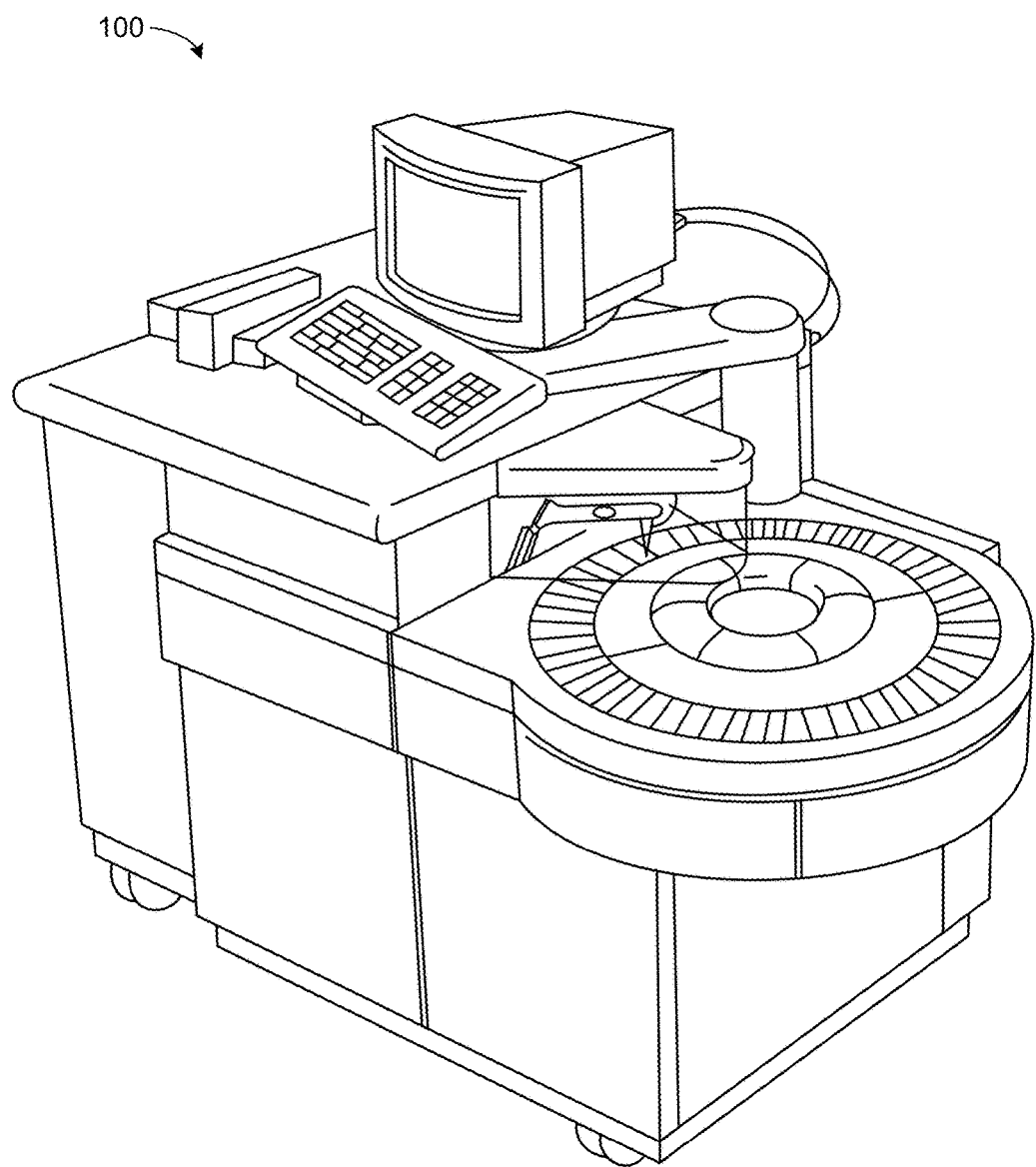
FIG. 1 illustrates an example automated analytical apparatus that may be implemented with an example liquid level sensing apparatus and related methods in accordance with the teachings of this disclosure.

Automated analytical apparatus (e.g., clinical chemistry and/or immunoassay diagnostic analyzers) rely on liquid level sensing to automate processing or testing of fluids (e.g., a biological fluid or sample), reagent liquids and/or buffer liquids contained or stored in containers or tubes. For example, detecting the presence of the liquid and/or locating a surface of the liquid permits controlled emersion of a pipetting apparatus into the liquid to enable a consistent amount of liquid volume to be aspirated or removed from a container. For example, known clinical analyzers typically employ liquid level sensing for use with open, uncapped containers. When an open, uncapped container is employed, a pipetting probe of the clinical analyzer may be positioned within the open-end container and a volume of the sample fluid may be aspirated or removed from the container.

Example liquid level sensing systems disclosed herein provide a pipetting system employing automated liquid level sensing capability. Specifically, example liquid level sensing systems disclosed herein may be used with automated analytical apparatus employing either open-end containers and/or closed or capped containers. Example liquid level sensing systems disclosed herein may include a pipetting system employing a pipetting probe to aspirate a liquid from a container and a cannula to pierce a septum or cap (e.g., a cover or top) of a container. In some examples, example pipetting systems disclosed herein enable a consistent amount of liquid volume to be aspirated or removed from a container. To detect the presence of the liquid and/or an amount or distance of emersion of the pipetting probe into the liquid, example liquid level sensing apparatus disclosed herein may be configured to emit or transmit a signal (e.g., a radio frequency signal) toward an antenna positioned adjacent the container.

In particular, to detect a liquid level of a container, example liquid level sensing apparatus disclosed herein may cause the pipetting probe to transmit a first signal. Additionally, to prevent the piercing cannula from degrading and/or otherwise interfering with a signal transmitted by the pipetting probe during level sense operation (e.g., when the pipetting probe is moving toward a liquid in a container), an example cannula disclosed herein may be configured to transmit a second signal. In some examples, the first signal is substantially the same (e.g., identical) to the second signal. In some examples, the first signal is different than, or phase-shift controlled relative to, the second signal. In some examples, the first signal and/or the second signal may have a frequency between approximately 0.3 Hz and 300 GHz. In some examples, the first signal and/or the second signal may be a digital signal and/or any other type of signal. For example, the first signal and/or the second signal may be digital pulse signal and/or any other type of signal modulation. In some examples, the first signal and/or the second signal may have a frequency between approximately a DC potential and 300 GHz.

In some examples, example liquid level sensing systems disclosed herein may include a phase-lock loop (e.g., an analog phase-lock loop, a digital phase-lock loop, etc.) for frequency generation, improved frequency stability and alignment (e.g., to maintain a relationship such as a phase-shift relationship, an equivalent relationship) between the first signal and the second signal. Thus, a phase-lock loop control system may be employed for signal phase integrity and/or noise and jitter control.

Example liquid level sensing systems disclosed herein electrically energize a cannula and the pipetting probe with electrically phase controlled signals. For example, a signal source (e.g., an oscillator) may provide electrically in-phase signals (e.g., the same signals or frequency, or a signal or frequency having a predetermined phase shift) to the cannula and the pipetting probe so that the pipetting probe and the cannula emit signals that are substantially the same or controlled (e.g. via phase shift).

In this manner, the pipetting probe and/or the piercing cannula may be composed of an electrically conductive material (e.g., a metallic material) to enable repeated piercing of containers without causing damage the cannula and without the cannula interfering or degrading the signal emitted by the pipetting probe when the pipetting probe is disposed in a container to detect a level of a liquid. As a result, the energized piercing cannula disclosed herein may puncture (e.g., vertically puncture) a top or cap of a closed container and the energized pipetting probe may be positioned through a channel or opening of the energized piercing cannula at similar or equal electrical potential (e.g., electrically phase controlled) without electrical impediment of the signal transmitted by the pipetting probe as the pipetting probe makes coordinated contact with liquid in the container.

An antenna (e.g. a transmitting or receiving antenna) may be positioned near or adjacent the container to receive or transmit the detected signal transmitted by the pipetting probe and/or the cannula, which may be analyzed for indication of contact with liquid in the container. In some examples, if the signal emitted by the cannula is phase controlled (e.g., radiates a frequency or signal having a phase shift) compared to the signal emitted by the probe, the antenna and/or a signal analyzer may be configured to differentiate (e.g., filter) the signal emitted by the probe and the signal emitted by the cannula. In addition, example liquid sensing systems disclosed herein maintain integrity of liquid level sensed during a descent of an electrically conductive pipetting probe through an electrically conductive piercing cannula that has pierced a closed or capped container. In some examples, an example piercing cannula disclosed herein may be energized using a wire to carry the signal (e.g., a radio frequency signal) from, for example, a signal source (e.g., a signal generator, a printed circuit board, etc.) to the piercing cannula. In some examples, the piercing cannula is energized using capacitive coupling to provide a connection between the signal source, the piercing cannula and/or the probe.

FIG. 1 is an example automated analytical apparatus (e.g., an immunoassay analytical system) in accordance with the teachings of this disclosure. The analytical system 100 of the illustrated example provides an automated continuous and/or random access analytical system, capable of simultaneously effecting multiple assays of a plurality of liquid samples. The analytical system 100 of the illustrated example includes a user input or interface to enable a user and/or other control system to input information or commands to the analytical system 100. In some examples, the example liquid level sensing apparatus disclosed herein may be retrofitted with existing analytical systems employed in the field. For example, the liquid level sensing apparatus disclosed herein may retrofit a system disclosed in U.S. Pat. No. 5,627,522, which is incorporated herein by reference in its entirety.

Figure 2:
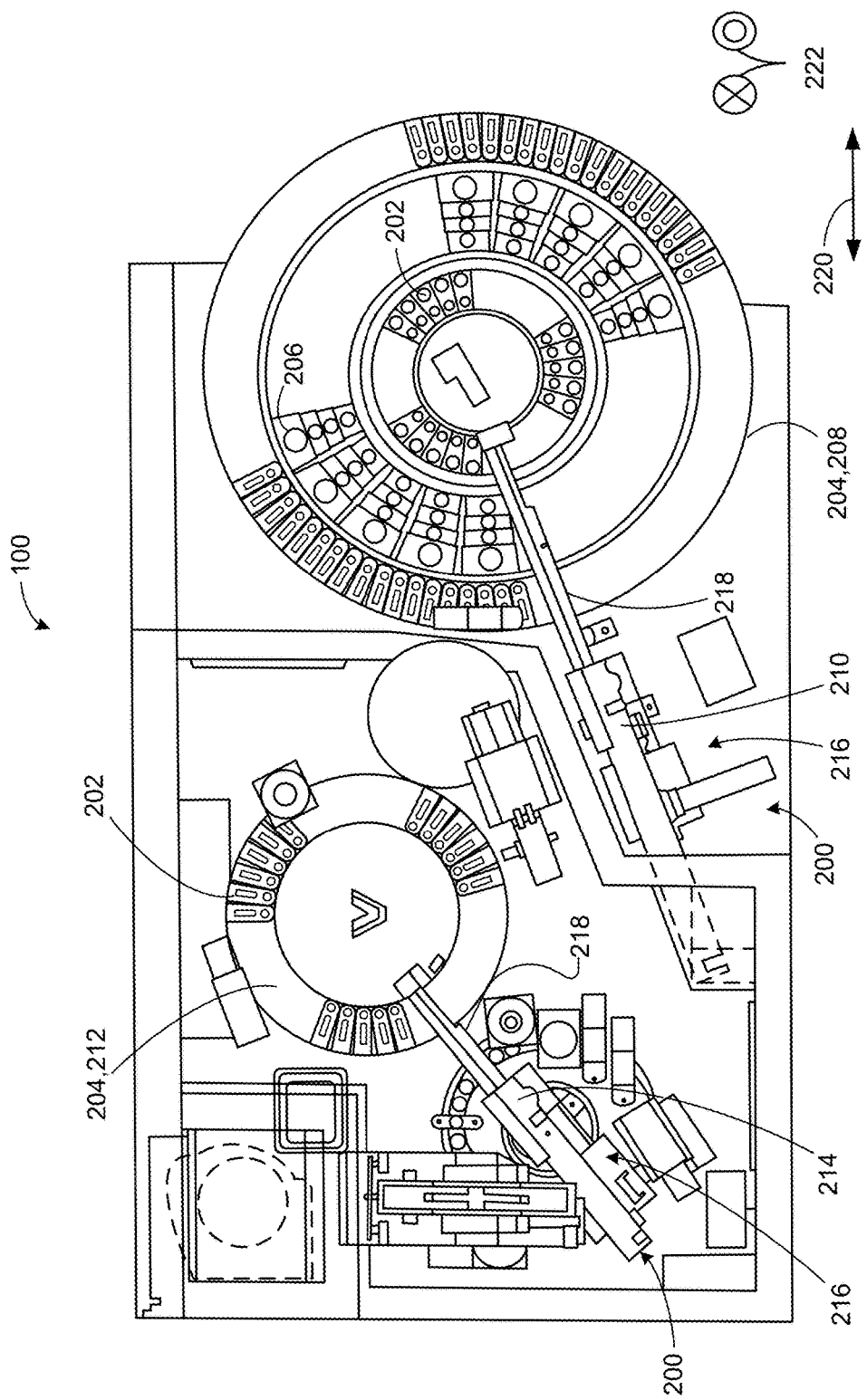
FIG. 2 illustrates a top plan view of a portion of the automated analytical apparatus illustrated example pipette system implemented with the example liquid level sensing apparatus and related methods disclosed herein.

FIG. 2 is plan view of the analytical system 100 of FIG. 1. The example analytical system 100 of the illustrated example employs a pipetting system 200 (e.g., a robotic arm pipetting system) employing an example liquid level system in accordance with the teachings of this disclosure. The pipetting system 200 obtains fluid from containers 202 held by a rotating carousel 204. The containers 202 may include sample containers, reagent containers, and/or any other container. The containers 202 of the illustrated example may include a (e.g., pierceable) septum or cover 206 that covers an opening of the containers 202 (e.g., caps, lids, etc.). The example analytical system 100 of FIGS. 1 and 2 includes a first carousel 208 that is serviced by a first pipetting system 210 and a second carousel 212 that is serviced by a second pipetting system 214. The first pipetting system 210 and/or the second pipetting system 214 may employ the example liquid sensing system disclosed herein. To move (e.g., aspirate or deliver) fluids relative to the containers 202, the first pipetting system 210 and the second pipetting system 214 include a drive system 216. The drive system 216 of the illustrated example includes a translatable arm or guide 218 to move a probe or cannula relative to the containers 202 positioned in the first carousel 208 or the second carousel 212 in a first direction 220 (e.g., a horizontal direction) and a second direction 222 (e.g. a vertical direction, which would be into and out of the paper or screen in the orientation shown in FIG. 2) that is different than the first direction 220 in the orientation of FIG. 2. For example, the translatable arm or guide 218 may include a first telescopically extending arm to move the cannula and/or the probe in the first direction 220 relative to the containers 202, a second telescopically extending arm to move the cannula in the second direction 222, and a third telescopically extending arm (e.g., slidable within the second telescopically extending arm) to move the probe in the second direction 222. The third telescopically extending arm may be configured to move the probe independently of the second telescopically extending arm of the cannula.

Figure 3:
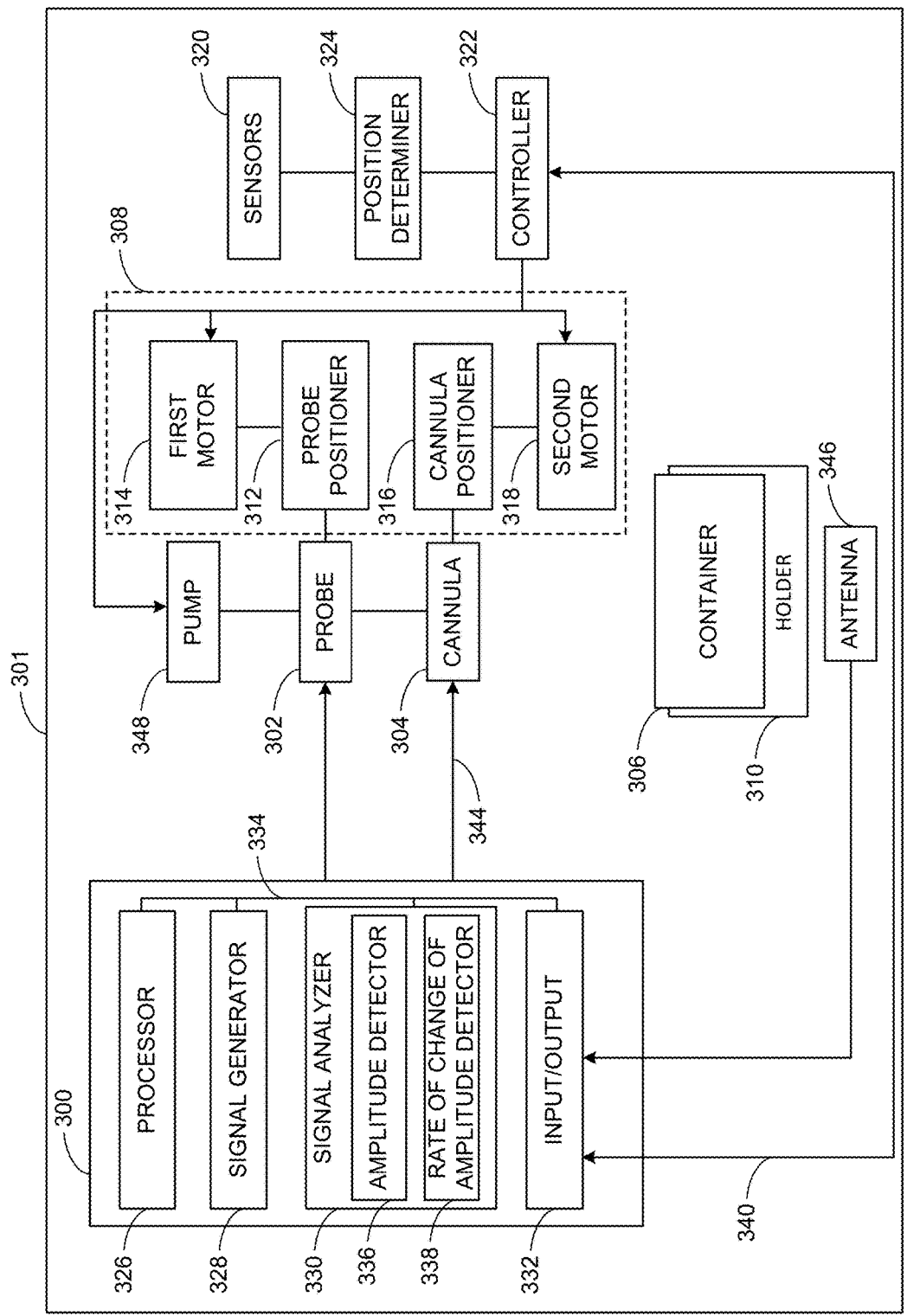
FIG. 3 is a block diagram of an example liquid level sensing apparatus in accordance with the teachings of this disclosure.

FIG. 3 is a block diagram of an example pipetting system 301 implemented with an example liquid level sensing system 300 in accordance with the teachings of this disclosure. For example, the example pipetting system 301 and/or the liquid level sensing system 300 of the illustrated example may be used to implement the first pipetting system 104 and/or the second pipetting system 106 of the example analytical system 100 of FIGS. 1 and 2. It is to be understood that the liquid level sensing system 300 of the present invention can be utilized in any automated instrument where liquid level sensing is desired.

The pipetting system 301 of the illustrated example includes a pipetting probe 302 and a piercing cannula 304 that are movable relative to a container 306 (e.g., the container 202 of FIG. 2) via a drive system 308 (e.g., the drive system 216 of FIG. 2). For example, the pipetting probe 302 of the illustrated example transfers fluid to and/or from the container 306 (generically representing a container in a reaction vessel, a reagent pack, or a test container). In some examples, the container 306 may be supported by a holder 310. The container 306 may be, for example, a test tube or other containers having a closed end provided by, for example, a cap (e.g. having a septum). The piercing cannula 304 pierces or provides an access opening to a closed end of the container 306 to enable the pipetting probe 302 to be inserted in a cavity of the container 306. More specifically, the pipetting probe 302 passes through a passageway of the piercing cannula 304 to access the container 306.

The drive system 308 of the illustrated example includes a probe positioner 312, a first motor 314, a cannula positioner 316 and a second motor 318. The probe positioner 312 moves the pipetting probe 302 relative to the cannula 304 and/or the container 306 via the first motor 314. For example, the probe positioner 312 moves the pipetting probe 302 relative to the cannula 304 and/or the container 306 in the first direction (e.g., the vertical or up and down direction relative to an upper surface or cap of the container 306) and the second direction (e.g., the sideways or horizontal direction relative to an upper surface or cap of the container 306) different than the first direction. The cannula positioner 316 moves the piercing cannula 304 relative to the container 306 via the second motor 318. For example, the cannula positioner 316 moves the cannula 304 relative to the container 306 in a first direction (e.g., a vertical or up and down direction relative to an upper surface or cap of the container 306) and a second direction (e.g., a sideways or horizontal direction relative to an upper surface or cap of the container 306). The probe positioner 312 and/or the cannula positioner 316 may include a telescopically movable robotic arm (e.g., the guide 218 of FIG. 2) to move the pipetting probe 302 and/or the cannula 304 in the first direction and a telescopically extending arm to move the pipetting probe 302 and/or the cannula 304 in the second direction. In some examples, the probe positioner 312 is a dedicated telescoping arm that moves independently from the cannula positioner 316. In this manner, the probe positioner 312 can move the pipetting probe 302 in the first direction and/or the second direction relative to the cannula 304, and the cannula positioner 316 can move the cannula 304 in the first direction and/or the second direction relative to the pipetting probe 302.

To determine a position of the cannula 304 relative to the container 306 (e.g., an upper surface or cap of the container 306), the example pipetting system 301 employs one or more sensors 320. In some examples, the sensors 320 (e.g., optical sensors, infrared sensors, etc.) determine an amount or distance the cannula 304 has moved relative to an upper surface or end of the container 306. In some examples, the sensors 320 detect or measure a distance between an end of the cannula and the upper end of the container 306 (e.g., a closed container). In some examples, the sensors 320 detect the presence of the container 306 and/or an upper surface of the container 306. In some such examples, the sensors 320 sense when the cannula 304 engages and/or pierces the upper surface (e.g., a septum or cap) of the container 306. In some examples, the sensors 320 determine when the cannula 304 has penetrated the container 306 and is positioned in the cavity at a predetermined distance relative to the upper surface of the container 306.

To control the operation of the probe positioner 312 via the first motor 314 and the cannula positioner 316 via the second motor 318, the example pipetting system 301 of the illustrated example employs a controller 322. For example, the controller 322 commands the second motor 318 to move the cannula 304 in the first direction and/or the second direction via the cannula positioner 316, and the controller 322 commands the first motor 314 to move the pipetting probe 302 in the first direction and/or the second direction via the probe positioner 312. To provide information regarding a position of the pipetting probe 302 and/or a position of the cannula 304 relative to the container 306 (e.g., an upper surface of the container 306), the pipetting system 301 of the illustrated example employs a position determiner 324. The position determiner 324 may receive one or more signals from sensors 320 providing feedback information regarding a position of the pipetting probe 302 and/or a position of the cannula 304 relative to the container 306. For example, the position determiner 324 determines a position of the pipetting probe 302, a position of the cannula 304, and/or a position of the container 306 and communicates this information to the controller 322. The controller 322, in turn, controls the movement of the pipetting probe 302 and/or the cannula 304 based on the position information provided by the position determiner 324. For example, the controller 322 may prevent or stop operation of the first motor 314 until the position determiner 324 determines that the cannula 304 has pierced the container 306 and/or is positioned inside the container 306. After the position determiner 324 determines that the cannula 304 is inside the container 306, the controller 322 may cause or command the first motor 314 to operate the probe positioner 312 and cause the probe 302 to move inside the container 306 (e.g., via an access opening of the cannula 304). In some examples, the controller 322 commands the second motor 318 to stop movement of the cannula 304 when the position determiner 324 determines that the cannula 304 is inside a cavity of the container 306.

To determine when the pipetting probe 302 engages a fluid (e.g., a biological sample or a reagent) in the container 306, the pipetting system 301 of the illustrated example employs the liquid level sensing system 300. The liquid level sensing system 300 of the illustrated example includes a processor 326, a signal generator 328, a signal analyzer 330, and an input/output interface 332 that are communicatively coupled via a field bus 334. The signal analyzer 330 of the illustrated example includes an amplitude detector 336 and a rate of change of amplitude detector 338. In some examples, however, the signal analyzer 330 of the illustrated example includes the amplitude detector 336. The liquid level sensing system 300 is communicatively coupled to the controller 322 via a wired and/or wireless communication channel or communication link 340.

In the illustrated example, the signal generator 328 electrically energizes the pipetting probe 302 and the cannula 304 with an electrically phase controlled signal. In some examples, the signal generator 328 of the illustrated example electrically energizes the pipetting probe 302 and the cannula 304 upon movement of the pipetting probe 302 via the probe positioner 312 and/or the cannula 304 via the cannula positioner 316. For example, the controller 322 may communicate or command the signal generator 328 via the input/output interface 332 and the communication link 340 to electrically energize the pipetting probe 302 and/or the cannula 304. In some examples, the controller 322 communicates or commands the signal generator 328 to electrically energize the pipetting probe 302 and/or the cannula 304 after at least a portion of the cannula 304 is positioned or disposed inside (e.g., has pierced) the container 306 and prior to movement of the pipetting probe 302 toward the container 306.

The signal generator 328 of the illustrated example electrically energizes the pipetting probe 302 to provide a first signal 342 to the pipetting probe 302 and electrically energizes the cannula 304 to provide a second signal 344 to the cannula 304. For example, each of the pipetting probe 302 and the cannula 304 emits or transmits a radio frequency signal when the first signal 342 is provided to the pipetting probe 302 and the second signal 344 is provided to the cannula 304. In some examples, the first signal 342 provided to the pipetting probe 302 is electrically in-phase with the second signal 344 provided to the cannula 304. In some examples, the first signal 342 may be identical to the second signal 344. For example, the first signal 342 of the pipetting probe 302 and the second signal 344 of the cannula 304 may each emit a signal having a frequency of approximately 125 kHz (e.g., plus or minus 10%). In some examples, the first signal 342 and/or the second signal 344 may have a frequency between approximately 0.3 Hz (or alternatively a DC potential) and 300 GHz. In some examples, the first signal 342 may be shifted out of phase (e.g., 90 degree phase shift, a 45 degree phase shift, or any other phase shift value) relative to the second signal 344. For example, the first signal 342 may lag the second signal 344 by a predetermined phase shift. In some examples, the first signal 342 and/or the second signal 344 may have a waveform including a sine wave, a square wave, a triangular wave, a sawtooth wave, etc. In some examples, the signal generator 328 may include a first signal generator to generate the first signal 342 to the pipetting probe 302 and a second signal generator to generate the second signal 344 to the cannula 304. The signal generator 328 of the illustrated example is a low impedance driver signal source.

In some examples, the signal generator 328 and, more generally, the example liquid level sensing system 300 may include a phase-lock loop control system for frequency generation, improved frequency stability and alignment between the first signal 342 and the second signal 344. For example, the phase-lock loop circuit maintains a relationship between the signal of the cannula 304 and the signal of the pipetting probe 302. In some examples, the phase-lock loop circuit maintains the electrically phase controlled electrical potential between the signal of the cannula 304 and the signal of the pipetting probe 302. In some examples, a phase-lock loop circuit may include a voltage-controlled oscillator, a phase detector, a low-pass filter, a variable-frequency oscillator and a feedback that may include a frequency divider.

The liquid level sensing system 300 of the illustrated example detects when the pipetting probe 302 contacts a fluid (e.g., a liquid) inside a cavity of the container 306. To determine when the pipetting probe 302 contacts the fluid in the container 306, the example liquid level sensing system 300 employs the signal analyzer 330. More specifically, as the pipetting probe 302 moves through the cannula 304 and/or inside the cavity of the container 306 and relative to the liquid in the container 306, the liquid level sensing system 300 detects changes in the signal (e.g., the near-radio frequency (RF) signal) that is radiated by the pipetting probe 302 and received by an antenna 346 positioned adjacent the container 306 (e.g., an antenna or a plurality of antennas positioned adjacent the rotating carousel of FIG. 2 or adjacent the container 306). The antenna 346 of the illustrated example is communicatively coupled to the signal analyzer 330 via the input/output interface 332 to transmit the received signal to the signal analyzer 330. For example, the signal analyzer 330 continually monitors the signal of the pipetting probe 302 as the pipetting probe 302 moves through an air-filled portion (e.g., a non-liquid filled portion) of the container 306 above the liquid and detects a change in signal and a rate of change in signal to detect the signal of the pipetting probe 302 when the pipetting probe 302 contacts the liquid in the container 306. The signal analyzer 330 (e.g., via a comparator) detects a change in the signal in response to the pipetting probe 302 contacting the liquid in the container 306 compared to the signal emitted by the pipetting probe 302 when the pipetting probe 302 is moving through the air-filled portion of the container 306 above the liquid (e.g., not in contact with the liquid 400).

More specifically, the amplitude detector 336 detects a change in the amplitude of the signal received by the antenna 346 as the pipetting probe 302 moves relative to the cannula 304 and/or the container 306. The rate of change of amplitude detector 338 detects a rate of signal change received by the antenna 346 as the pipetting probe 302 moves through the air-filled portion towards the liquid filled portion. For example, both the amplitude detector 336 and the rate of change of amplitude detector 338 detect a change in the amplitude of the signal received by the antenna 346 as the pipetting probe 302 moves through the air (e.g., not in engagement with liquid in the container 306) and when the pipetting probe 302 comes into direct engagement with liquid in the container 306. The example signal analyzer 330 determines the presence of liquid when both the amplitude detector 336 and the rate of amplitude detector 338 receive a signal indicative of the pipetting probe 302 coming into contact with the liquid. Basing liquid detections on both signal amplitude and rate of change of signal amplitude reduces the number of false or failed liquid detections. However, as the pipetting probe 302 contacts liquid in the container 306, the amplitude of the signal generated by the pipetting probe 302 increases or, in other words, has a positive slope. Thus, for a given frequency of, for example, 125 kHz, the amplitude of the signal received by the antenna 346 may be greater than an amplitude of a system noise envelope when the pipetting probe 302 engages the liquid. The amplitude detector 336 detects a change in the amplitude of the detected signal as the pipetting probe 302 moves relative to the cannula 304 and/or the container 306. To prevent false detections, the rate of change of amplitude detector 338 detects a change in the slope between the amplitude of the signal received by the antenna 346 and the slope of the system noise envelope. In this manner, if the slope of the detected change of amplitude is not greater than a threshold, the rate of change of amplitude detector 338 determines that the pipetting probe 302 has not contacted the liquid. If the slope is greater than a threshold, the rate of change of amplitude detector 338 determines that the pipetting probe 302 contacted the liquid. In some examples, the signal analyzer does not include the rate of change of amplitude detector 338 and instead only detects liquid when the amplitude detector 336 detects a change in the amplitude of a detected signal.

To remove or aspirate a volume of fluid from the container 306 when the liquid level sensing system 300 determines that the pipetting probe 302 is in contact with the liquid in the container 306, the pipetting system 301 of the illustrated example employs a pump 348 (e.g., a syringe). For example, the liquid level sensing system 300 may be configured to send a signal to the controller 322 to activate the pump 348. The controller 322 may command the first motor 314 and the second motor 318 to operate the probe positioner 312 and the cannula positioner 316 to remove the pipetting probe 302 and the cannula 304 from the container 306 after an amount of fluid is aspirated by the pipetting probe 302.

The liquid level sensing system 300 enables the energized pipetting probe 302 to be positioned through a channel or opening of the energized piercing cannula 304 at an electrically phase controlled electrical potential (e.g., similar or equal frequency, controlled out of phase shift frequency, etc.) without electrical impediment of the signal emitted or transmitted by the pipetting probe 302 as the pipetting probe 302 makes coordinated contact with liquid in the container 306 while being adjacent (e.g., passing through) the cannula 304. As noted above, a phase-lock loop control system may be employed for signal phase integrity and/or jitter control.

While an example manner of implementing the pipetting system 301 is illustrated in FIG. 3, one or more of the elements, processes and/or devices illustrated in FIG. 3 may be combined, divided, re-arranged, omitted, eliminated and/or implemented in any other way. Further, the example liquid level sensing apparatus 300, the example probe positioner 312, the example cannula positioner 316, the example controller 322, the example positioner determiner 324, the example processor 326, the example signal generator 328, the example signal analyzer 330, the example amplitude detector 336, the example rate of change of amplitude detector 338, the example input/output interface 332 and/or, more generally, the example pipetting system 301 of FIG. 3 may be implemented by hardware, software, firmware and/or any combination of hardware, software and/or firmware. Thus, for example, any of the example liquid level sensing apparatus 300, the example probe positioner 312, the example cannula positioner 316, the example controller 322, the example positioner determiner 324, the example processor 326, the example signal generator 328, the example signal analyzer 330, the example amplitude detector 336, the example rate of change of amplitude detector 338, the example input/output interface 332 and/or, more generally, the example pipetting system 301 of FIG. 3 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example liquid level sensing apparatus 300, the example probe positioner 312, the example cannula positioner 316, the example controller 322, the example positioner determiner 324, the example processor 326, the example signal generator 328, the example signal analyzer 330, the example amplitude detector 336, the example rate of change of amplitude detector 338, the example input/output interface 332 and/or, more generally, the example pipetting system 301 of FIG. 3 is/are hereby expressly defined to include a non-transitory computer readable storage device or storage disk such as a memory, a digital versatile disk (DVD), a compact disk (CD), a Blu-ray disk, etc. including the software and/or firmware. Further still, the example pipetting system 301 of FIG. 3 may include one or more elements, processes and/or devices in addition to, or instead of, those illustrated in FIG. 3, and/or may include more than one of any or all of the illustrated elements, processes and devices.

Figure 4:
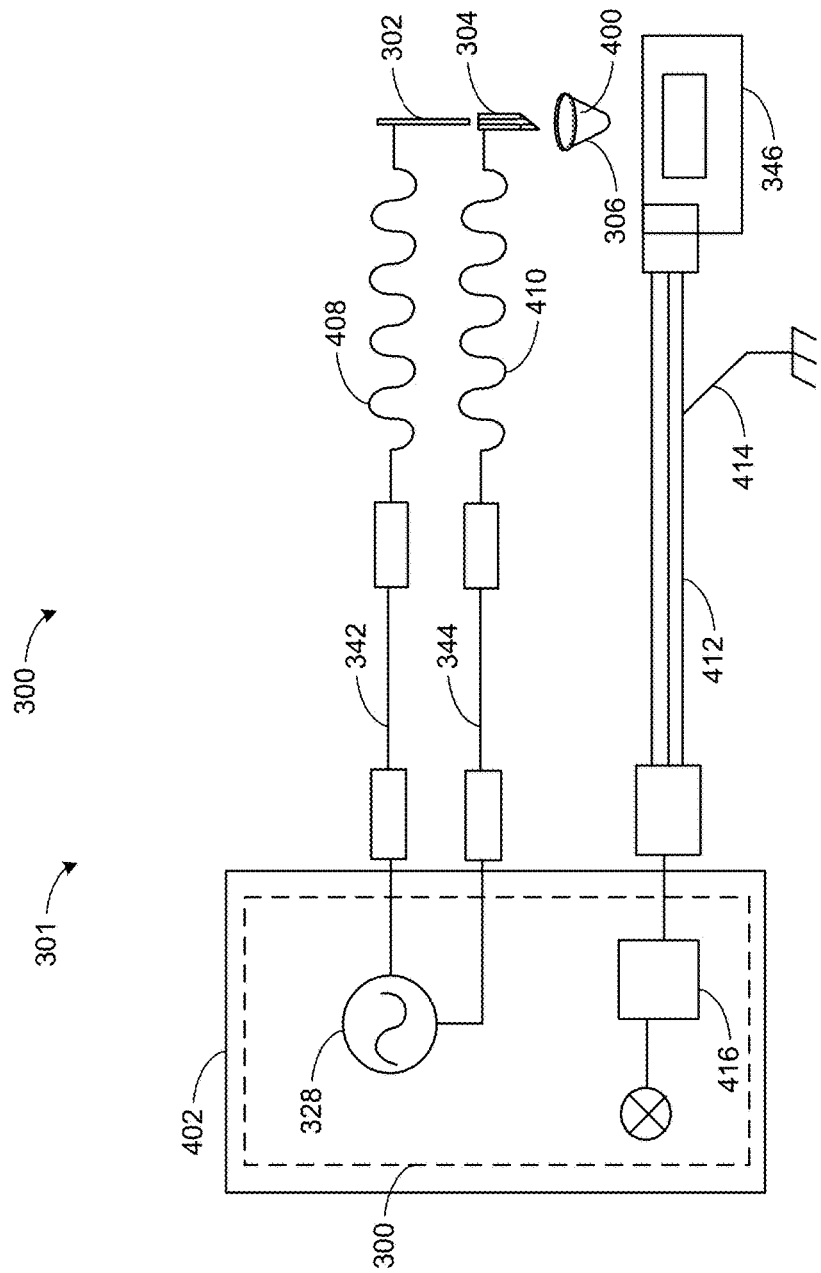
FIG. 4 is a schematic illustration of the example liquid level sensing apparatus of FIG. 3.

FIG. 4 is a schematic illustration of the example pipetting system 301 and the example liquid level sensing system 300 of FIG. 3 to detect or sense a level of a liquid 400 in the container 306 via the pipetting probe 302 when using the cannula 304 to pierce the container 306. The liquid level sensing system 300 includes a circuit board 402 (e.g., a printed circuit board) that includes the signal generator 328 to provide or generate the first signal 342 to the pipetting probe 302 and the second signal 344 to the cannula 304. In some examples, the circuit board 402 is configured to receive approximately +5 Volts.

The first signal 342 generated by the signal generator 328 is transmitted to the pipetting probe 302 via a connector or first cable 408 (e.g., a coax cable). Similarly, the second signal 344 generated by the signal generator 328 is transmitted to the cannula 304 via a second connector or second cable 410 (e.g., a coax cable). In some examples, a phase-locked loop control system may be employed for frequency generation, improved frequency stability and alignment between the first signal 342 and the second signal 344.

In some examples, neither the pipetting probe 302 nor the cannula 304 are grounded. In some examples, both the pipetting probe 302 and the cannula 304 are grounded. The antenna 346 of the illustrated example is communicatively coupled to the liquid level sensing system 300 via a connector or cable 412 (e.g., a coaxial cable). The antenna 346 of the illustrated example is grounded via a ground 414. The antenna 346 is mounted or positioned in a stationary position beneath an area where liquid sensing is desired (e.g., beneath the container 306). In some examples, the antenna 346 includes a plurality of antennas positioned below the rotating carousel 204 of the analytical system 100 of FIG. 1. The antenna 346 transmits the received signal from the pipetting probe 302 to the liquid level sensing system 300 via the cable 412. The example liquid level sensing system 300 of the illustrated example may employ a shield circuit 416 as described in greater detail in connection with FIG. 10.

FIG. 5 illustrates the pipetting system 301 in a first position 500 (e.g., a stationary or initial position). Referring to FIG. 5, the cannula 304 of the illustrated example includes a body 502 (e.g., a cylindrical body) having a first end 504 and a second end 506 opposite the first end 504. The cannula 304 includes a channel or opening 508 to form an access or passageway 510 between the first end 504 and second end 506 (e.g., between an exterior of the container 306 and an interior of the container 306). The first end 504 of the cannula 304 of the illustrated example includes a cannula tip 512 (e.g., an angled tip) to facilitate piercing or puncturing a seal 514 (e.g., a cap) positioned at a first end 516 of the container 306 to provide access to a cavity 518 of the container 306 (e.g., a sealed container). The seal 514 of the illustrated example may include a septum that may be pierced (e.g., repeatedly pierced) by the cannula 304. The pipetting probe 302 of the illustrated example is a hollow tube that passes through the passageway 510 of the cannula 304. The cannula 304 and the pipetting probe 302 of the illustrated example are composed of electrically conductive material or combination of materials. For example, the cannula 304 and/or the pipetting probe 302 may be composed of aluminum, stainless steel, an alloy and/or any other electrically conductive material(s). The antenna 346 is positioned adjacent (e.g., underneath) a second end 520 of the container 306 opposite the first end 516. In the first position 500 of FIG. 5, the pipetting probe 302 and the cannula 304 are spaced away (e.g., vertically spaced) from the container 306 such that neither the cannula 304 nor the pipetting probe 302 are in direct contact with the seal 514 and/or the container 306. Further, in the example first position 500 of FIG. 5, the first signal 342 and the second signal 344 is not provided to the pipetting probe 302 and cannula 304.

FIG. 6 illustrates the pipetting system 301 in a second position 600. For example, in the second position 600 of FIG. 6, the liquid level sensing system 300 and/or the pipetting system 301 received a command to obtain a sample of liquid 400 from the cavity 518 of the container 306. In response to receiving the command, the signal generator 328 provides the first signal 342 to the pipetting probe 302 and the second signal 344 to the cannula 304. The pipetting probe 302 of the illustrated example is composed of an electrically conductive material to enable the pipetting probe 302 to emit the first signal 342 and/or the cannula 304 of the illustrated example is composed of an electrically conductive material to enable the cannula 304 to emit the second signal 344. When electrically charged or energized with the first signal 342, the pipetting probe 302 emits a first electrical field 602 relative to a longitudinal axis 604 of the pipetting probe 302. When the cannula 304 is electrically charged or energized with the second signal 344, the cannula 304 emits a second electrical field 606 relative to a longitudinal axis 608 of the cannula 304.

The first signal 342 radiated by the probe traverses or radiates across the air space between the pipetting probe 302 and the antenna 346. The first signal 342 is coupled from the pipetting probe 302 to the antenna 346 primarily by the first electrical field 602. Because the first electrical field 602 is actually part of an electromagnetic field radiating from the pipetting probe 302, the liquid level sensing system 300 may also be referred to as an "RF" (radio frequency) sensing system, although in some examples an actual frequency employed by the first signal 342 (e.g., 125 kHz) may be several octaves below standard radio frequencies. When the pipetting probe 302 and the cannula 304 are positioned in the air, the antenna 346 receives a relatively weak or small signal (e.g., a null) from the first electrical field 602 along the extension of the longitudinal axis 604 of the pipetting probe 302 and/or the second electrical field 606 along the extension of the longitudinal axis 608 of the cannula 304.

Further, because the cannula 304 of the illustrated example radiates the second electrical field 606 provided by the second signal 344 (e.g., which may be identical or substantially similar to the first signal 342), the cannula 304 when composed of an electrically conductive material does not interfere or degrade the first electrical field 602 and/or the first signal 342 emitted or transmitted by the pipetting probe 302 when the pipetting probe 302 passes through the passageway 510 or is otherwise positioned adjacent the cannula 304. Absent the second signal 344, the cannula 304, when composed of an electrically conductive material, may degrade or otherwise interfere with the first signal 342 radiated by the pipetting probe 302 when the pipetting probe 302 passes through the passageway 510 or is positioned adjacent the cannula 304. Electrically grounding only the cannula 304 would not help prevent degradation of the first signal 342 because an electrically grounded cannula 304 attracts or shields the first signal 342 radiated by the pipetting probe 302 instead of enabling the first signal 342 to radiate toward the antenna 346 along the longitudinal axis 604 of the pipetting probe 302 if the pipetting probe 302 is not also grounded. Thus, in some examples, neither the pipetting probe 302 nor the cannula 304 are grounded. In some examples, both the pipetting probe 302 and the cannula 304 is grounded or at a DC potential.

When the liquid level sensing system 300 receives a command to obtain a sample of the liquid 400 in the container 306, the controller 322 commands the second motor 318 to operate the cannula positioner 316. To position the cannula 304 in the cavity 518 of the container 306, the position determiner 324 receives positional information representative of a position of the cannula 304 relative to the container 306 from the sensors 320. For example, the position determiner 324 determines the position of the container 306 relative to the cannula 304 and commands the cannula positioner 316 to move in a first direction (e.g., horizontally) via the second motor 318 to align with the container 306. The sensors 320 detects the position of the seal 514, and the controller 322 commands the second motor 318 to move in a second direction (e.g., vertically) toward the seal 514 via the cannula positioner 316. The sensors 320 detect when the cannula 304 is immediately adjacent (e.g., in direct contact with) an upper surface 614 of the seal 514 and communicates this information to the controller 322. The controller 322 may command or cause the second motor 318 to stop after a certain period of time lapses from the time of detection of the cannula 304 being adjacent the upper surface 614 of the seal 514. For example, the position determiner 324 may instruct the controller 322 to command the second motor 318 to stop after 3 milliseconds from the time the position determiner 324 detects the cannula tip 512 being in direct contact with the upper surface 614 of the seal 514 to ensure that the cannula tip 512 pierces the seal 514 and at least partially enters the cavity 518 of the container 306. Thus, the cannula tip 512 of the cannula 304 is at least partially positioned in the cavity 518 or the container 306 when the cannula 304 pierces the container 306. In some examples, the sensors 320 may detect when the cannula 304 has pierced through the seal 514 and is positioned in the cavity 518. After the cannula 304 has pierced the seal 514, the controller 322 commands or causes the second motor 318 to stop (e.g., remove power to the second motor 318).

Figure 7:
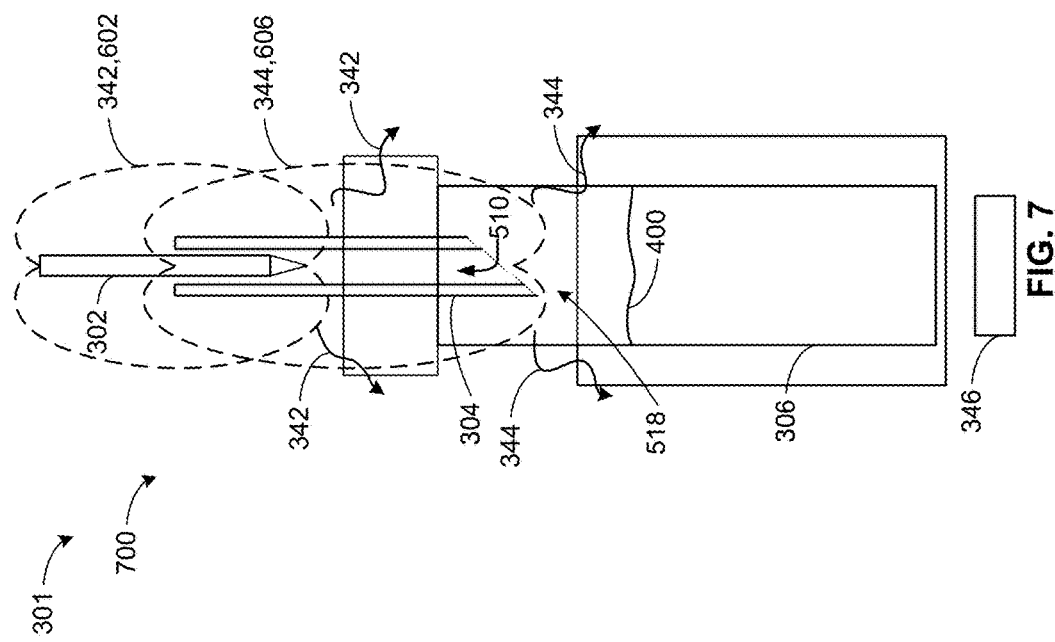

FIG. 7 illustrates the pipetting system 301 in a third position 700. In the third position 700 of FIG. 7, the pipetting probe 302 is positioned in the passageway 510 of the cannula 304. For example, the controller 322 may command or cause the first motor 314 to operate to move the pipetting probe 302 (e.g., vertically) toward the container 306 via the probe positioner 312. As shown in FIG. 7, although the cannula 304 is composed of a metallic or electrically conductive material, the first electrical field 602 generated by the first signal 342 through the pipetting probe 302 is not affected by the cannula 304 because the second signal 344 is radiating the second electrical field 606 through the cannula 304. In some instances, the second signal 344 of the cannula 304 may prevent degradation of the first signal 342 emitted by the pipetting probe 302.

Figure 8:
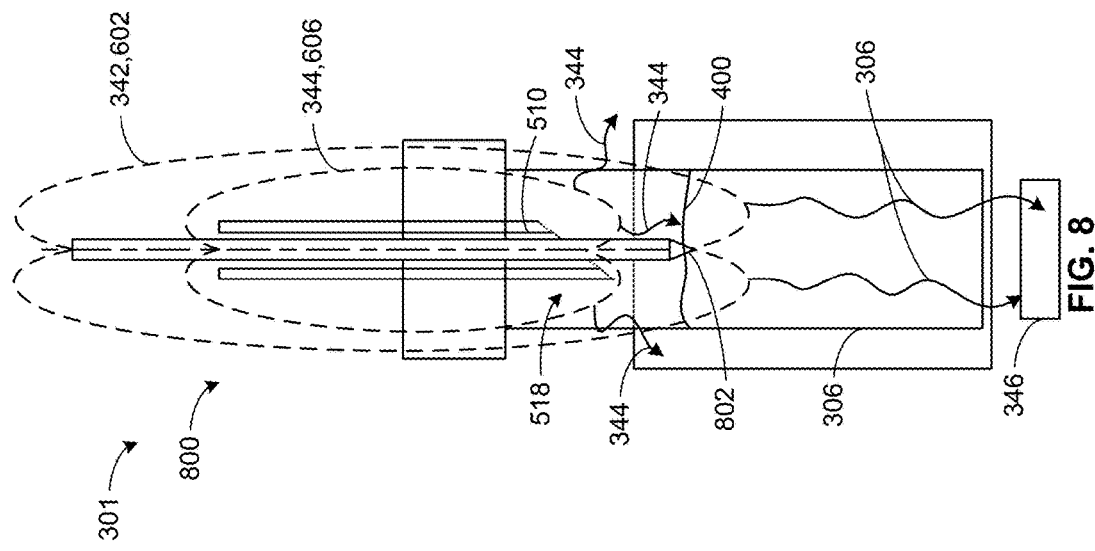

FIG. 8 illustrates the pipetting system 301 in a fourth position 800. In the example fourth position 800 of FIG. 8, the pipetting probe 302 contacts the liquid 400 in the cavity 518 of the container 306 via the passageway 510 provided by the cannula 304. In particular, the liquid level sensing system 300 determines when the pipetting probe 302 contacts the liquid 400 and provides a signal to the controller 322 to command or cause the first motor 314 to stop (e.g., remove power to the first motor 314). In operation, when the pipetting probe 302 is lowered in the cavity 518 of the container 306 and contacts the liquid 400, the first signal 342 from the pipetting probe 302 to the antenna 346 increases or is greater (e.g., a greater intensity) than a signal received by the antenna 346 from the pipetting probe 302 when the pipetting probe 302 is in air (e.g., not in contact with the liquid 400 in the cavity 518). The signal increases because the liquid 400 in the container 306, in effect, propagates the signal transmitted by the pipetting probe 302 by directing the electromagnetic field of the pipetting probe 302 toward the receiving antenna 346. In other words, the amplitude of the received first signal 342 is greater when the pipetting probe 302 contacts the liquid 400 than when the pipetting probe 302 is not in contact with the liquid 400. The antenna 346 receives a stronger signal (e.g., a signal with a greater amplitude) transmitted by the pipetting probe 302 when the pipetting probe 302 is in contact with the liquid 400 and communicates the signal to the signal analyzer 330.

In turn, signal analyzer 330, via the amplitude detector 336 and the rate of change of amplitude detector 338, determines if the pipetting probe 302 contacts the liquid 400. As noted above, the amplitude detector 338 detects a spike or change in amplitude provided by the first signal 342 when compared to, for example, a system noise envelope, and amplitude of the first signal 342 when the pipetting probe 302 is not in direct contact with the liquid 400, etc. The rate of change of amplitude detector 338 prevents false positives by analyzing a slope of a curve of the amplitude detected by the amplitude detector 338 to determine if the detected slope is greater than a threshold. The rate of change of amplitude detector 338 detects whether the slope of the amplitude detected by the amplitude detector 336 is greater than a threshold and communicates this result to the signal analyzer 330. The signal analyzer 330 determines that the pipetting probe 302 has contacted the liquid 400 based on the signal provided by the antenna 346 when an amplitude is detected and a rate of change of the amplitude detected is greater than a threshold. As a result, the example liquid level sensing system 300 detects contact with the liquid 400 upon a tip 802 of the pipetting probe 302 contacting the liquid 400. For example, when the pipetting probe 302 contacts the liquid 400 in the container 306, a signal propagates through the liquid 400. The signal to the cannula 304 helps prevent degradation of the signal that enters or broadcasted by the pipetting probe 302 when, for example, the cannula 304 is composed of an electrically conductive material. Thus, the second signal 344 to the cannula 304 helps promote the first signal 342 through the pipetting probe 302 to reach the antenna 346.

When the signal analyzer 330 determines that the pipetting probe 302 is in contact with the liquid 400 (e.g., using the amplitude detector 336 and/or the rate of change of amplitude detector 338), the signal analyzer 330 instructs the controller 322 to stop operation of the first motor 314 (e.g., remove power to the first motor 314). The controller 322 instructs the pump 348 to activate to enable a sample of the liquid 400 in the cavity 518 of the container 306 to be aspirated in the hollow body of the pipetting probe 302. Once the pump 348 has activated to obtain the sample, the controller 322 commands the first motor 314 to move the pipetting probe 302 via the probe positioner 312 away from the liquid 400 and/or the container 306. After the pipetting probe 302 is removed from the container 306 and/or the passageway 510 of the cannula 304, the controller 322 commands the second motor 318 to move the cannula 304 via the cannula positioner 316 away from the container 306 so that the cannula 304 is removed from the cavity 518 and/or spaced from the upper surface 614 of the seal 514.

Alternatively, as noted above, the example pipetting system 301 may be configured with other types of signals to provide liquid level detection. For example, the pipetting system 301 may be configured with a digital signal to sense when the pipetting probe 302 contacts the liquid 400 (e.g., using a DC potential). For example, the pipetting probe 302 and the cannula 304 may be provided with substantially the same voltage. In some such examples, the signal generator 328 may be configured to provide a voltage to the pipetting probe 302 and the cannula 304 representative of the first signal 342 and the second signal 344, respectively. For example, the pipetting probe 302 emits an electrostatic field potential (e.g., the first signal 342) that is substantially similar to an electrostatic field potential (e.g., the second signal 344) emitted by the cannula 304 as the pipetting probe 302 passes through the cannula 304 because the same voltage is applied to the cannula 304 and the pipetting probe 302. Thus, in operation, the voltage or the first signal 342 applied to the pipetting probe 302 will not be affected when the pipetting probe 302 passes through the cannula 304 and/or through the air-filled portion of the container 306. When the pipetting probe 302 contacts the liquid 400, the electrostatic field emitted by the pipetting probe 302 shifts or changes (e.g., increases in amplitude). The change in the electrostatic field is sensed or received by the antenna 346. For example, a change in the DC potential of the first signal 342 is detected when the pipetting probe 302 moves through the air-filled portion (e.g., a non-liquid filled portion) of the container 306 above the liquid and when the pipetting probe 302 contacts the liquid 400. In turn, the signal analyzer 330, via the amplitude detector 336 and/or the rate of change of amplitude detector 338, determines if the pipetting probe 302 contacts the liquid 400. For example, to determine when the pipetting probe 302 directly engages or contacts the liquid 400, the signal analyzer 330 detects a shift or change (e.g., in amplitude) of the electrostatic field potential provided by the first signal 342 of the pipetting probe 302 when compared to, for example, (e.g., an amplitude of) the electrostatic field potential provided by the first signal 342 when the pipetting probe 302 is not in direct contact with the liquid 400.

Figure 9:
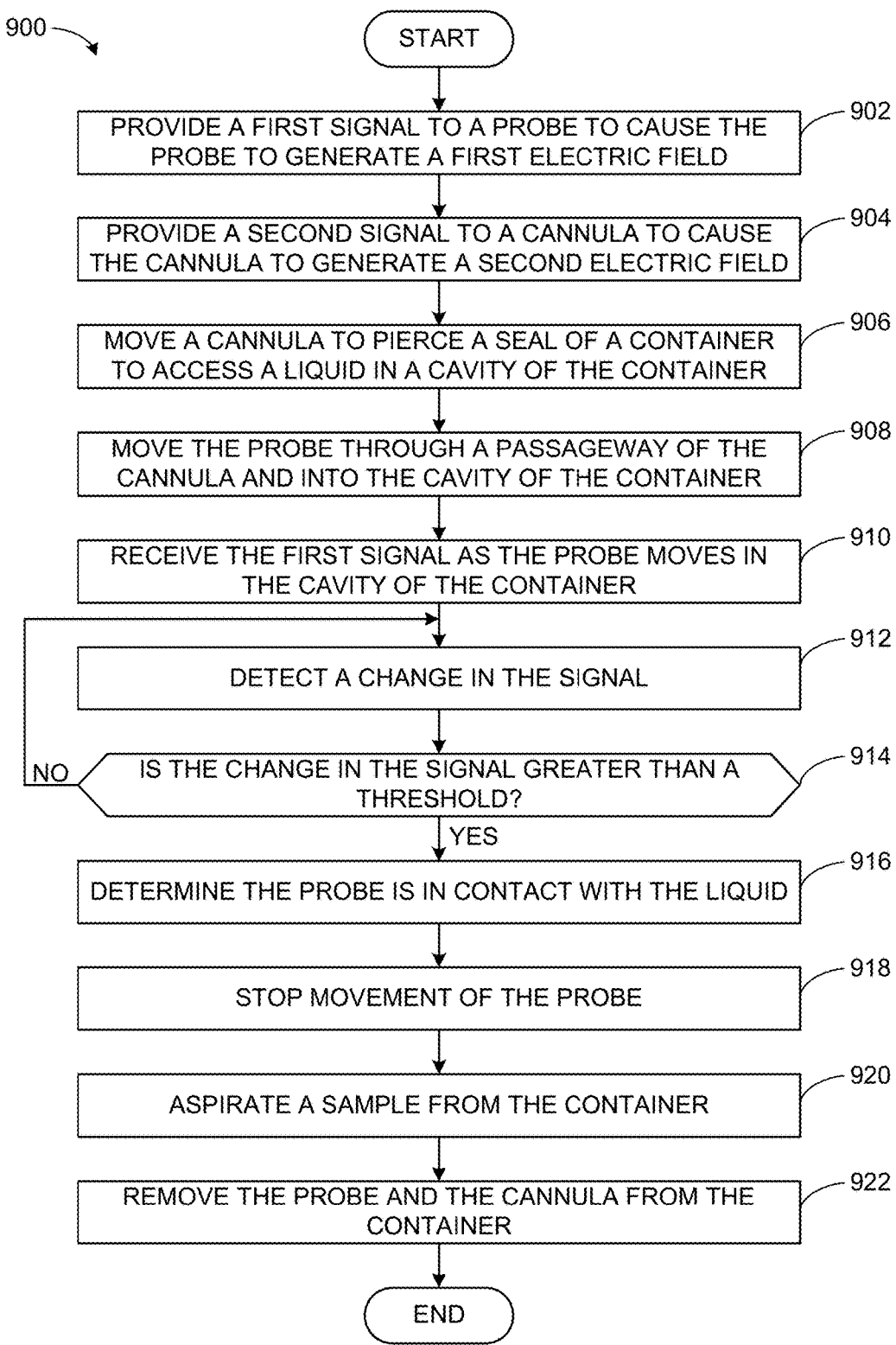
FIG. 9 is a flowchart representative of an example method of implementing the example liquid level sensing apparatus of FIGS. 3-8.

A flowchart 900 representative of example machine readable instructions for implementing the liquid level sensing system 300 and/or the pipetting system 301 of FIGS. 3-8 is shown in FIG. 9. In this example, the machine readable instructions comprise a program for execution by a processor such as the processor 1012 shown in the example processor platform 1000 discussed below in connection with FIG. 10. The program may be embodied in software stored on a non-transitory computer readable storage medium such as a CD-ROM, a floppy disk, a hard drive, a digital versatile disk (DVD), a Blu-ray disk, or a memory associated with the processor 1012, but the entire program and/or parts thereof could alternatively be executed by a device other than the processor 1012 and/or embodied in firmware or dedicated hardware. Further, although the example program is described with reference to the flowchart illustrated in FIG. 9, many other methods of implementing the example liquid level sensing system 300 and/or the pipetting system 301 may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, a Field Programmable Gate Array (FPGA), an Application Specific Integrated circuit (ASIC), a comparator, an operational-amplifier (op-amp), a logic circuit, etc.) structured to perform the corresponding operation without executing software or firmware.

As mentioned above, the example processes of FIG. 9 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. "Including" and "comprising" (and all forms and tenses thereof) are used herein to be open ended terms. Thus, whenever a claim lists anything following any form of "include" or "comprise" (e.g., comprises, includes, comprising, including, etc.), it is to be understood that additional elements, terms, etc. may be present without falling outside the scope of the corresponding claim. As used herein, when the phrase "at least" is used as the transition term in a preamble of a claim, it is open-ended in the same manner as the term "comprising" and "including" are open ended.

The example program of FIG. 9 includes providing a first signal (e.g. the RF signal) to a probe to cause the probe to generate the first electrical field (block 902). For example, the signal generator 328 may be instructed or commanded to apply the first signal 342 to the pipetting probe 302 when the controller 322 receives a command to obtain a sample of liquid 400 from the cavity 518 of the container 306.

The example program 900 also includes providing a second signal (e.g. a RF signal) to a cannula to cause the cannula to generate a second electrical field (block 904). In some examples, the signal generator 328 provides the second signal 304 to the cannula 344 to cause the cannula 304 to generate the second electrical field 606. In some examples, the first signal 342 provided to the pipetting probe 302 by the signal generator 328 is substantially the same (e.g., within plus or minus 10%) or identical to the second signal 344 provided to the cannula 304 by the signal generator 328. In some examples, the first signal 342 provided by the signal generator 328 is shifted out of phase relative to the second signal 344 generated by the signal generator 328.

The example program 900 includes causing a cannula to pierce a seal of a container to provide an access to a liquid in the container (block 906). For example, the controller 322 may cause or command the second motor 318 to move the cannula 304 toward the container 306 via the cannula positioner 316 until the cannula tip 512 pierces or passes through the seal 514 and into the cavity 518 of the container 306.

The example program 900 includes moving a probe through a passageway of the cannula and into the cavity of the container (block 908). For example, the controller 322 may cause or command the first motor 314 to move the pipetting probe 302 relative to the container 306 via the probe positioner 312 and toward the liquid 400 in the container 306 through the passageway 510 of the cannula 304.

The example program 900 includes receiving, via an antenna, the first signal generated by the probe as the probe moves into the cavity of the container (block 910). For example, the first signal 342 applied to the pipetting probe 302 generates the first electrical field 602 that is detected or received by the antenna 346 as the pipetting probe 302 moves into the cavity 518.

A signal analyzer detects a change in the first signal (block 912). The signal analyzer determines if the first signal is greater than a threshold (block 914). For example, the signal analyzer 330 employs the amplitude detector 336 to detect a change (e.g., an increase or decrease) in an amplitude of the first signal 342 and the rate of change of amplitude detector 338 to detect a rate of change (e.g., a rate of increase or decrease) of the detected first signal 342. For example, the amplitude detector 336 determines an amplitude of the first signal 342 compared to, for example, a slope of a system noise envelope of the analytical system 100. If the amplitude is greater than a threshold (e.g., a detected magnitude of the first signal 342 being greater than 10 percent of a magnitude of the slope of the system noise envelope curve), then the amplitude detector 336 determines that an amplitude change has occurred. When an amplitude change has occurred, the rate of change of amplitude detector 338 detects if a slope between the curve of the system noise envelope and a peak of the amplitude detected when the change occurred is greater than a threshold.

If the signal analyzer determines that the change in the detected first signal is not greater than a threshold at block 914, then the process returns to block 912. If the signal analyzer determines that the change in the detected first signal is greater than the threshold at block 914, the signal analyzer determines that the probe is in contact with the liquid in the container (block 916). Thus, the liquid level sensing system 300 of the illustrated example determination that the pipetting probe 302 engages the liquid 400 is based on detection of both a signal amplitude detected by the amplitude detector 336 and a rate of change of signal amplitude detected by the rate of change of amplitude detector 338. In other words, it is determined that the pipetting probe 302 has contacted the liquid 400 when both the signal amplitude and the rate of signal change indicate that the amplitude change and rate of change has occurred.

The controller stops movement of the probe when the probe is determined to be in contact (e.g., direct contact) with the liquid in the container (block 918). For example, the controller 322 commands or causes the first motor 314 to stop by removing power to the first motor 314.

A liquid sample from the container is then aspirated (block 920). For example, with the tip 802 of the pipetting probe 302 in the liquid 400 after the first motor 314 is commanded to stop, the controller 322 activates the pump 348 to aspirate a sample of the liquid 400 in the container 306.

After the liquid is aspirated, the probe and the cannula are removed from the container (block 922). For example, the controller 322 commands or causes the first motor 314 to operate to cause the pipetting probe 302 to move away from the container 306 via the probe positioner 312 and the controller commands or causes the second motor 318 to operate to cause the cannula 304 to move away from the container 306 via the cannula positioner 316.

The example liquid level sensing system 300 disclosed herein may be used in any automated instrument where liquid level sensing is desired.

Figure 10:
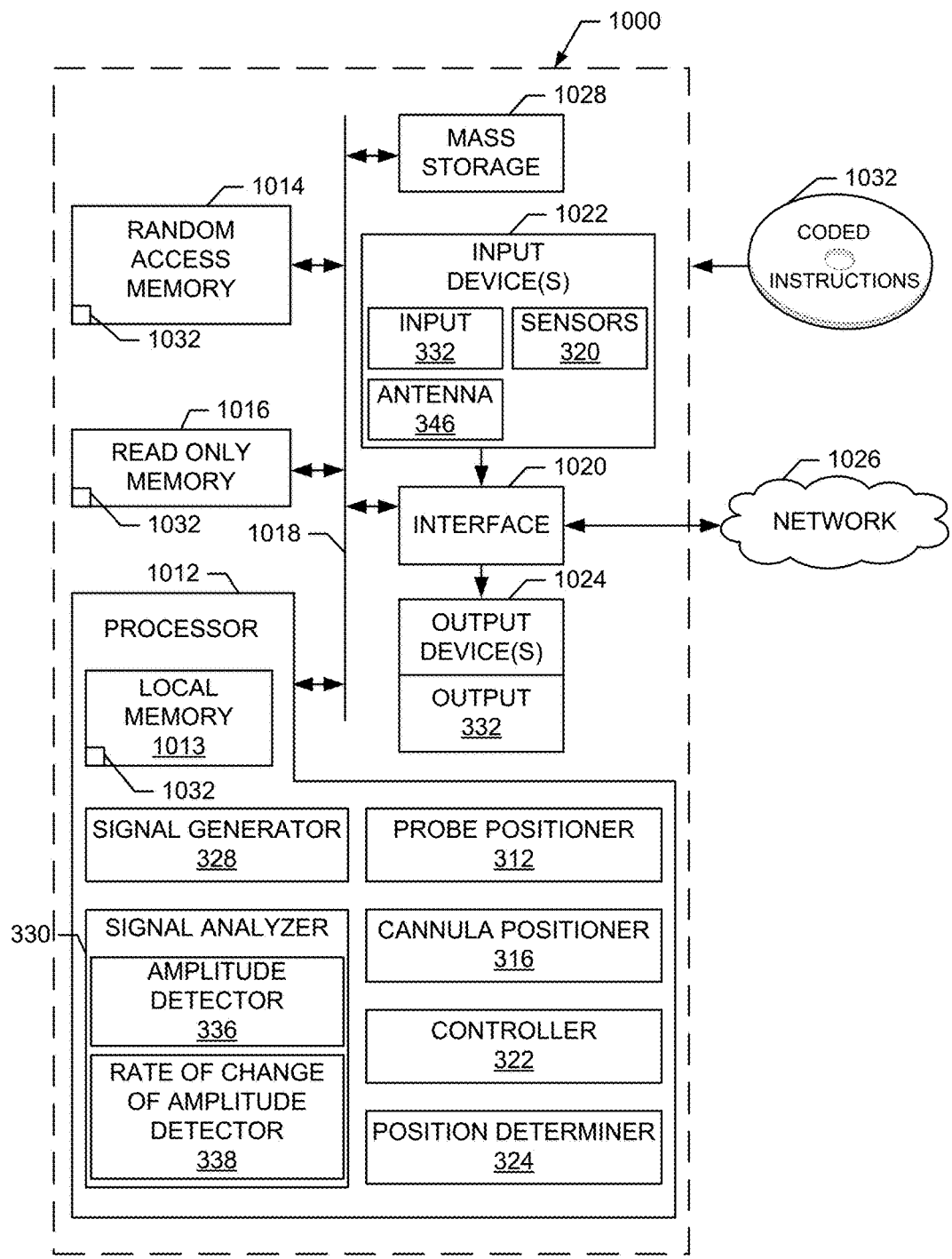
FIG. 10 is a block diagram of an example processor platform capable of executing the instructions of FIG. 9 implementation of the liquid level sensing apparatus of FIG. 3.

FIG. 10 is a block diagram of an example processor platform 1000 capable of executing the instructions of FIG. 9 to implement the liquid level sensing system 300 or the pipetting system 301 of FIG. 3. The processor platform 1000 can be, for example, a server, a personal computer, a mobile device (e.g., a cell phone, a smart phone, a tablet such as an iPad™), a personal digital assistant (PDA), an Internet appliance or any other type of computing device.

The processor platform 1000 of the illustrated example includes a processor 1012. The processor 1012 of the illustrated example is hardware. For example, the processor 1012 can be implemented by one or more integrated circuits, logic circuits, microprocessors or controllers from any desired family or manufacturer. The hardware processor may be a semiconductor based (e.g., silicon based) device. In this example, the processor implements the example liquid level sensing apparatus 300, the example probe positioner 312, the example cannula positioner 316, the example controller 322, the example positioner determiner 324, the example processor 326, the example signal generator 328, the example signal analyzer 330, the example amplitude detector 336, the example rate of change of amplitude detector 338, the example input/output interface 332 and/or, more generally, the example pipetting system 301.

The processor 1012 of the illustrated example includes a local memory 1013 (e.g., a cache). The processor 1012 of the illustrated example is in communication with a main memory including a volatile memory 1014 and a non-volatile memory 1016 via a bus 1018. The volatile memory 1014 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1016 may be implemented by flash memory and/or any other desired type of memory device. Access to the main memory 1014, 1016 is controlled by a memory controller.

The processor platform 1000 of the illustrated example also includes an interface circuit 1020. The interface circuit 1020 may be implemented by any type of interface standard, such as an Ethernet interface, a universal serial bus (USB), and/or a PCI express interface.

In the illustrated example, one or more input devices 1022 are connected to the interface circuit 1020. The input device(s) 1022 permit(s) a user to enter data and/or commands into the processor 1012. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 1024 are also connected to the interface circuit 1020 of the illustrated example. The output devices 1024 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 1020 of the illustrated example, thus, typically includes a graphics driver card, a graphics driver chip and/or a graphics driver processor.

The interface circuit 1020 of the illustrated example also includes a communication device such as a transmitter, a receiver, a transceiver, a modem and/or network interface card to facilitate exchange of data with external machines (e.g., computing devices of any kind) via a network 1026 (e.g., an Ethernet connection, a digital subscriber line (DSL), a telephone line, coaxial cable, a cellular telephone system, etc.).

The processor platform 1000 of the illustrated example also includes one or more mass storage devices 1028 for storing software and/or data. Examples of such mass storage devices 1028 include floppy disk drives, hard drive disks, compact disk drives, Blu-ray disk drives, RAID systems, and digital versatile disk (DVD) drives.

The coded instructions 1032 of FIG. 10 may be stored in the mass storage device 1028, in the volatile memory 1014, in the non-volatile memory 1016, and/or on a removable tangible computer readable storage medium such as a CD or DVD.

At least some of the aforementioned examples include one or more features and/or benefits including, but not limited to, the following:

In some examples, an example liquid level sensing apparatus includes a cannula defining a body having a tip and an access channel. The tip is to pierce a container. The cannula is to be at least partially positioned in the container when the tip pierces the container. In some such examples, a probe is to be positioned in the access channel. In some such examples, a signal source is to electrically energize the probe and the cannula to cause the probe to emit a first signal and cause the cannula to emit a second signal.

In some examples, the first signal is electrically phase controlled relative to the second signal.

In some examples, the first and second signals are controlled via phase-lock loop control system.

In some examples, an antenna is adjacent the container to detect a transmission of the first signal when the probe contacts a liquid in the container and the probe is positioned through the access channel of the cannula.

In some examples, the cannula and the probe are composed of an electrically conductive material.

In some examples, the first signal and the second signal are radio frequency signals.

In some examples, the second signal emitted by the cannula is to prevent degradation of the first signal emitted by the probe when the probe is positioned in the access channel of the cannula.

In some examples, the cannula does not interfere with the first signal emitted by the probe.

In some examples, neither the probe nor the cannula are electrically grounded.

In some examples, the first signal is electrically in phase with the second signal.

In some examples, the first signal is electrically phase shifted from the second signal.

In some examples, both the probe and the cannula are electrically grounded.

In some examples, at least one of the first signal or the second signal includes a waveform having a sine wave, a square wave, a triangular wave, or a sawtooth wave.

In some examples, an example liquid level sensing apparatus includes a cannula composed of a conductive material. In some such examples, the cannula is to pierce a seal of a container. In some such examples, the cannula is movable relative to the container in a first direction and a second direction, where the first direction being different than the second direction. In some such examples, the cannula includes an opening passing through a first end of the cannula and a second end of the cannula to define a passageway. In some such examples, the cannula is to emit a first signal when at least a portion of the cannula is positioned in a cavity of the container. In some such examples, a probe is composed of a conductive material. In some such examples, the probe is movable relative to the cannula in the first direction and the second direction, where the probe to emit a second signal. In some such examples, the probe is to pass through the passageway provided by the cannula to aspirate a sample from the container. In some such examples, a signal generator operatively couples to the cannula and the probe. In some such examples, the signal generator is to provide the first signal to the cannula and the second signal to the probe.

In some examples, the first signal is electrically in phase with the second signal.

In some examples, the first signal is electrically phase shifted from the second signal.

In some examples, neither the probe nor the cannula are electrically grounded.

In some examples, both the probe and the cannula are electrically grounded.

In some examples, an antenna is to receive the second signal of the probe when the probe is inside the container and the passageway of the cannula.

In some examples, the cannula is to emit the first signal while the probe is moving through the passageway of the cannula.

In some examples, the first signal emitted by the cannula is to prevent degradation of the second signal emitted by the probe when the probe is positioned in the passageway of the cannula.

In some examples, a method for sensing liquid in a container includes providing a first signal to a probe to cause the probe to emit a first electrical field. In some such examples, the method includes providing a second signal to a cannula to cause the cannula to emit a second electrical field. In some such examples, the method includes moving the cannula to pierce a seal of a container to provide an access to a liquid in a cavity of the container. In some such examples, the method includes moving the probe through a passageway of the cannula and into the cavity of the container while the probe emits the first electrical field and the cannula emits the second electrical field.

In such examples, the method includes positioning an antenna adjacent a bottom surface of the container, the antenna to receive the first signal emitted by the probe.

In some such examples, the method includes detecting a change in the first signal and determining if the detected change in the first signal is greater than a threshold.

In some such examples, the method includes stopping movement of the probe when the detected change in the first signal is greater than the threshold.

In some such examples, the method includes electrically grounding neither the probe nor the cannula.

In some such examples, the method includes electrically grounding both the probe and the cannula.

In some examples, a non-transitory computer-readable medium includes instructions that, when executed, cause a machine to: provide a first signal to a probe to cause the probe to emit a first electrical field; provide a second signal to a cannula to cause the cannula to emit a second electrical field; move the cannula to pierce a seal of a container to provide an access to a liquid in a cavity of the container; and move the probe through a passageway of the cannula and into the cavity of the container while the probe emits the first electrical field and the cannula emits the second electrical field.

In some examples, the instructions when executed, further cause the machine to receive the first signal emitted by the probe via an antenna positioned adjacent a bottom surface of the container.

In some examples, the instructions when executed, further cause the machine to detect a change in the first signal and determine if the detected change in the first signal is greater than a threshold.

In some examples, the instructions when executed, further cause the machine to stop movement of the probe when the detected change in the first signal is greater than the threshold.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A liquid sensing apparatus comprising:
   a cannula defining a body having a tip and an access channel, the tip configured to pierce a container, the cannula configured to be at least partially positioned in the container when the tip pierces the container;
   a probe configured to be positioned in the access channel; and
   a signal source configured to independently electrically energize the probe and the cannula to cause the probe to emit a first signal and cause the cannula to emit a second signal when the probe is at least partially positioned in the access channel of the cannula.

2. The apparatus of claim 1, wherein the first signal is electrically phase controlled relative to the second signal.

3. The apparatus of claim 2, wherein the first and second signals are controlled via phase-lock loop control system.

4. The apparatus of claim 1, further including an antenna adjacent the container to detect a transmission of the first signal when the probe contacts a liquid in the container and the probe is positioned through the access channel of the cannula.

5. The apparatus of claim 1, wherein the cannula and the probe are composed of an electrically conductive material.

6. The apparatus of claim 1, wherein the first signal and the second signal are radio frequency signals.

7. The apparatus of claim 1, wherein the second signal emitted by the cannula is to prevent degradation of the first signal emitted by the probe when the probe is positioned in the access channel of the cannula.

8. The apparatus of claim 1, wherein the cannula does not interfere with the first signal emitted by the probe.

9. The apparatus of claim 1, wherein neither the probe nor the cannula are electrically grounded.

10. The apparatus of claim 1, wherein the first signal is electrically in phase with the second signal.

11. The apparatus of claim 1, wherein the first signal is electrically phase shifted from the second signal.

12. The apparatus of claim 1, wherein both the probe and the cannula are electrically grounded.

13. The apparatus of claim 1, wherein at least one of the first signal or the second signal includes a waveform having a sine wave, a square wave, a triangular wave, or a sawtooth wave.

14. The apparatus of claim 1, wherein the cannula is structured to pierce a seal of the container.

15. The apparatus of claim 1, wherein the cannula is movable relative to the container in a first direction and a second direction, the first direction being different than the second direction.

16. The apparatus of claim 15, wherein the cannula is configured to emit the second signal when at least a portion of the cannula is positioned in a cavity of the container.

17. The apparatus of claim 16, wherein the cannula includes an opening passing through a first end of the cannula and a second end of the cannula to define a passageway.

18. The apparatus of claim 17, wherein the probe is movable relative to the cannula in the first direction and the second direction.

19. The apparatus of claim 18, wherein the probe is configured to pass through the passageway provided by the cannula to aspirate a sample from the container.

20. The apparatus of claim 19, wherein the cannula is configured to emit the second signal while the probe is moving through the passageway of the cannula.

21. The apparatus of claim 20, wherein the second signal emitted by the cannula is to prevent degradation of the second signal emitted by the probe when the probe is positioned in the passageway of the cannula.

22. The apparatus of claim 21, further including an antenna to receive the second signal of the probe when the probe is inside the container and the passageway of the cannula.

23. A liquid sensing apparatus comprising:
   a cannula defining a body having a tip and an access channel, the tip configured to pierce a container, the cannula configured to be at least partially positioned in the container when the tip pierces the container;
   a probe configured to be positioned in the access channel; and
   a signal source configured to electrically energize the probe and the cannula at least when the probe is at least partially positioned in the access channel of the cannula, the signal source to provide a first signal to the probe to cause the probe to emit the first signal, the signal source to provide a second signal to the cannula to cause the cannula to emit the second signal.

24. The apparatus of claim 23, wherein the first signal is electrically phase controlled relative to the second signal.

25. The apparatus of claim 24, wherein the first and second signals are controlled via phase-lock loop control system.

26. The apparatus of claim 23, further including an antenna adjacent the container to detect a transmission of the first signal when the probe contacts a liquid in the container and the probe is positioned through the access channel of the cannula.

27. The apparatus of claim 23, wherein the cannula and the probe are composed of an electrically conductive material.

28. The apparatus of claim 23, wherein the first signal and the second signal are radio frequency signals.

29. The apparatus of claim 23, wherein the second signal emitted by the cannula is to prevent degradation of the first signal emitted by the probe when the probe is positioned in the access channel of the cannula.

30. The apparatus of claim 23, wherein the cannula does not interfere with the first signal emitted by the probe.

31. The apparatus of claim 23, wherein neither the probe nor the cannula is electrically grounded.

32. The apparatus of claim 23, wherein the first signal is electrically in phase with the second signal.

33. The apparatus of claim 23, wherein the first signal is electrically phase shifted from the second signal.

34. The apparatus of claim 23, wherein both the probe and the cannula are electrically grounded.

35. The apparatus of claim 23, wherein at least one of the first signal or the second signal includes a waveform having a sine wave, a square wave, a triangular wave, or a sawtooth wave.

36. The apparatus of claim 23, wherein the cannula is structured to pierce a seal of the container.

37. The apparatus of claim 23, wherein the cannula is movable relative to the container in a first direction and a second direction, the first direction being different than the second direction.

38. The apparatus of claim 37, wherein the cannula is configured to emit the second signal when at least a portion of the cannula is positioned in a cavity of the container.

39. The apparatus of claim 38, wherein the cannula includes an opening passing through a first end of the cannula and a second end of the cannula to define a passageway.

40. The apparatus of claim 39, wherein the probe is movable relative to the cannula in the first direction and the second direction.

41. The apparatus of claim 40, wherein the probe is configured to pass through the passageway provided by the cannula to aspirate a sample from the container.

42. The apparatus of claim 41, wherein the cannula is configured to emit the second signal while the probe is moving through the passageway of the cannula.

43. The apparatus of claim 42, wherein the second signal emitted by the cannula is to prevent degradation of the second signal emitted by the probe when the probe is positioned in the passageway of the cannula.

44. The apparatus of claim 43, further including an antenna to receive the second signal of the probe when the probe is inside the container and the passageway of the cannula.

* * * * *